US00PP35904P3

(12) United States Plant Patent
Arts

(10) Patent No.: US PP35,904 P3
(45) Date of Patent: Jul. 2, 2024

(54) RASPBERRY PLANT NAMED 'ABB 136'

(50) Latin Name: ***Rubus. idaeus* L**
Varietal Denomination: ABB 136

(71) Applicant: Allberry B. V., JJ Hedel (NL)

(72) Inventor: Niels Arts, De Kwakel (NL)

(73) Assignee: Allberry B.V., J.J. Hedel (NL)

( * ) Notice: Subject to any disclaimer, the term of this patent is extended or adjusted under 35 U.S.C. 154(b) by 0 days.

(21) Appl. No.: 18/445,159

(22) Filed: May 2, 2023

(65) Prior Publication Data

US 2023/0422645 P1 Dec. 28, 2023

(30) Foreign Application Priority Data

May 4, 2022 (QZ) ..... PBR 20221159

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ..... A01H 5/08; A01H 5/00; A01H 6/7499; A01H 6/74
See application file for complete search history.

(56) References Cited

U.S. PATENT DOCUMENTS

PP23,914 P2 9/2013 Smaal et al.
RE46,030 E * 6/2016 Smaal ..... A01H 6/7499 Plt./204
PP27,583 P3 * 1/2017 Adams ..... Plt./204

* cited by examiner

*Primary Examiner* — June Hwu
(74) *Attorney, Agent, or Firm* — Hunt IP Law

(57) ABSTRACT

The new and distinct variety of raspberry plant variety 'ABB 136' is provided. The variety can be distinguished by its outstanding features of early double cropping, high productivity, light red color, and early second crop without chilling.

3 Drawing Sheets

Latin name of the genus and species:
Botanical classification:
a. Genus—*Rubus.*
b. Species—*idaeus* L.
Variety denomination: The new raspberry plant claimed is of the variety denominated 'ABB 136'.

CROSS REFERENCE TO RELATED APPLICATIONS

This application claims the benefit of priority under 35 USC § 119 to Community Plant Variety Office (CPVO) Application No. 20221159 for Community Plant Variety Rights, filed on May 4, 2022, for a raspberry plant with a variety denomination of 'ABB 136', which is herein incorporated by reference in its entirety.

BACKGROUND OF THE INVENTION

Field of the Invention

The present invention relates to a new and distinct annual variety of raspberry plant, which has been given the variety denomination of 'ABB 136'.

Background of the Related Art

Raspberries are the edible fruit of a multitude of plant species in the genus *Rubus* of the rose family. Most raspberry species are in the subgenus Idaeobatus. Raspberry plants are perennial plants with woody stems. Many of the most important modern commercial red raspberry cultivars derive from hybrids between *R. idaeus* and *R. strigosus.* Recent breeding has resulted in cultivars that are thornless and more strongly upright, not needing staking.

Both the red and the black raspberry species have albino like pale-yellow natural or horticultural variants. Fruits from such plants are called golden raspberries or yellow raspberries. Most pale-fruited raspberries commercially sold in the eastern United States are derivatives of red raspberries. Yellow-fruited variants of the black raspberry are sometimes grown in home gardens. Despite their dissimilar appearance, golden raspberries retain the distinctive flavor of their respective red or black species.

An individual raspberry fruit is made up of around 100 drupelets, each of which contains a juicy pulp and a single central seed. A raspberry bush can yield several hundred berries in a year. Unlike blackberries and dewberries, a raspberry has a hollow core once it is removed from the receptacle.

Raspberries are traditionally planted in the winter as dormant canes, but planting plugs produced by tissue culture is also common. Additionally, the long cane production method consists of growing canes for one year in cold climates where the bud break is early, and then transplanting the canes to warmer climates where they quickly flower and can produce an early season crop. A very vigorous crop, raspberries spread well and can be considered invasive, using extended underground shoots (also known as suckers or basal shoots) that can develop roots and individual plants.

Raspberries are a popular fruit that are recognized for their antioxidants, high fiber, and as a good source of vitamin C. Raspberry fruit is typically consumed as fresh fruit, individually quick frozen (IQF) fruit, or in prepared foods, such as purees, juices, jellies, jams, grocery items, baked goods, and snack foods.

Raspberry is an important and valuable commercial fruit crop, widely grown in all temperate regions of the world. Accordingly, there is a need for new varieties of raspberry plant. In particular, there is a need for improved varieties of raspberry plant that are stable, high yielding, and agronomically sound.

SUMMARY OF THE INVENTION

The present invention relates to a new and distinct annual variety of raspberry, which has been given the variety denomination of 'ABB 136' and is intended for use as fresh fruit.

The new raspberry variety is a selection resulting from a sexual cross of raspberry plants at De Kwakel in 2016, involving a seed parent known as 'Advabertwee' (U.S. Plant Pat. No. 23,914; U.S. Reissue Pat. No. 46,030) and a pollen parent known as '211157-6' (unpatented).

The selection was subsequently evaluated for a number of years at Rossum, Netherlands.

Asexual reproduction of the new variety by cutting propagation since 2018 at Rossum, Netherlands, has demonstrated that the new variety reproduces true to type with all of the morphological characteristics, as herein described, firmly fixed and retained through successive generations of such asexual propagation.

Selection criteria were earliness and productivity.

The following characteristics of the new variety have been repeatedly observed and can be used to distinguish 'ABB 136' as a new and distinct variety of raspberry plant: early double cropping, high productivity, light red fruit color, and early second crop without chilling.

Plants of the new variety differ from plants of the seed parent 'Advabertwee' as set forth in Table 1. As no plants of the pollen parent '211157-6' exist, and there are no similar varieties, no comparison to a pollen parent can be made. This variety differs from 'ABB 127' (U.S. Plant Pat. No. 33,576) by its natural ability to branch and its lower chill requirements.

TABLE 1

| Parental variety | Characteristics | Similar variety level of expression | Candidate variety level of expression |
|---|---|---|---|
| 'Advabertwee' | Plant vigor | Good | Very high |
| 'Advabertwee' | Primocane productivity | Medium-high | Very high |
| 'Advabertwee' | Fruit firmness | Very firm | Firm |

BRIEF DESCRIPTION OF THE DRAWINGS

The accompanying photographic illustrations show the typical appearance of the new variety 'ABB 136'. The colors are as nearly true as is reasonably possible in a color representation of this type. Colors in the photographs may differ slightly from the color values cited in the detailed botanical description which accurately describes the colors of the new plant.

DETAILED BOTANICAL DESCRIPTION

Figure 1:
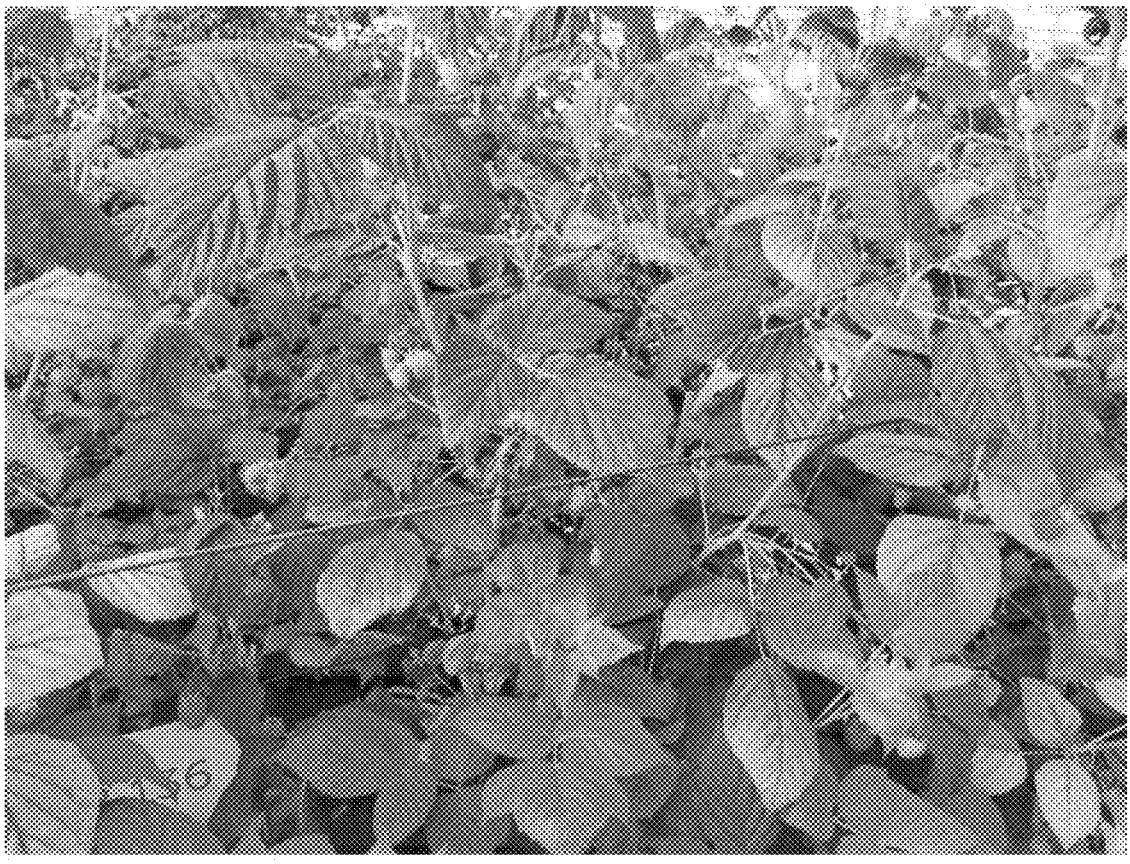
FIG. 1 is a photograph of the new variety 'ABB 136', demonstrating optimal budbreak and strong regrowth of second crop.
Figure 2:
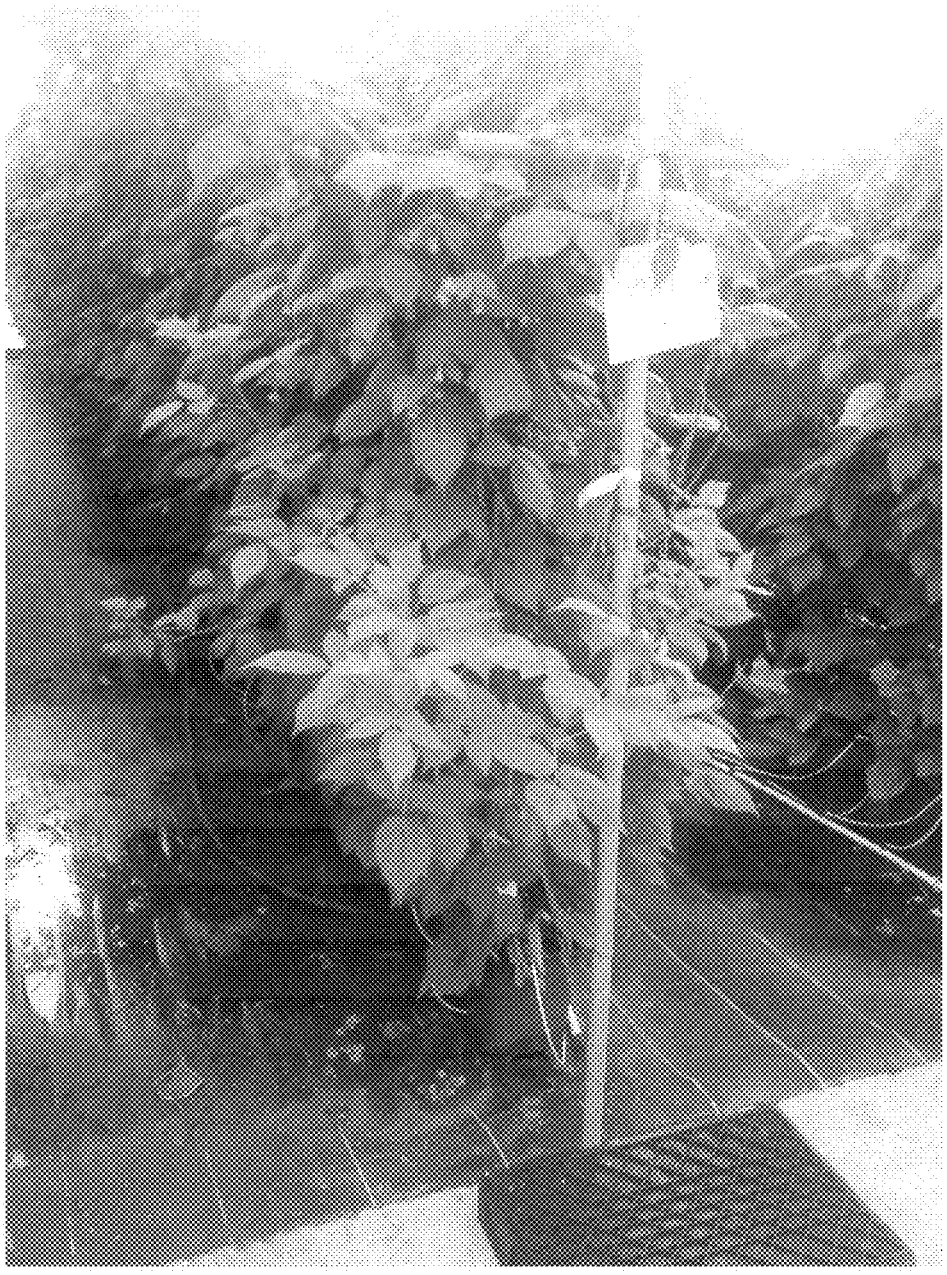
FIG. 2 is a photograph of the new variety 'ABB 136', demonstrating vigorous growth and high productivity at primocane stage.
Figure 3:
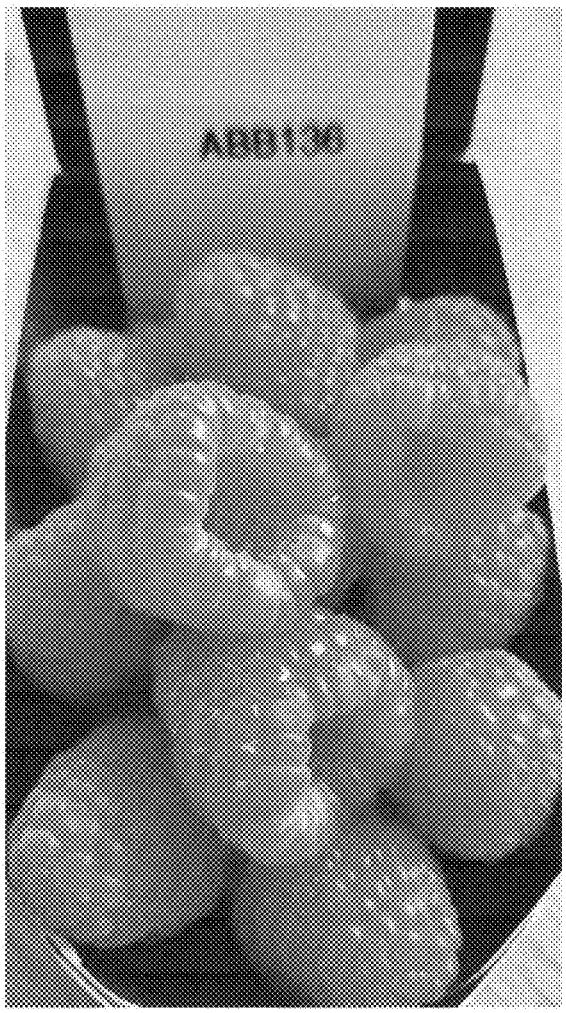
FIG. 3 is a photograph of fruit of the new variety 'ABB 136', at primocane production stage.

The following detailed description sets forth the distinctive characteristics of 'ABB 136'. The datum which defines these characteristics was collected from asexual reproductions of the original selection. Dimensions, sizes, colors, and other characteristics are approximations and averages set forth as accurately as possible. The plant history was taken on plants approximately 18 weeks, and the descriptions relate to plants grown in Rossum, Netherlands. Color notations are in reference to the standard R.H.S. Color Chart 2015.

Classification:

a. *Family.*—Rosaceae.
b. *Botanical.*—*Rubus idaeus* L.
c. *Common name.*—Raspberry.
d. *Variety name.*—'ABB 136'.

Parentage:

a. *Female parent.*—'Advabertwee' (U.S. Plant Pat. No. 23,914).
b. *Male parent.*—'211157-6'.

PLANT

General:

a. *Height.*—220-250 cm.
b. *Width.*—80-120 cm.
c. *Length/width ratio.*—Average.
d. *Growth habit.*—Semi upright.
e. *Primocane* (*current year's cane*).—i. Color — Green-135D. ii. Cane length in autumn — 220-250 cm. iii. Internodal distance at central ⅓ of cane — 7 cm. iv. Anthocyanin coloration of cane — Weak. v. Cane bloom — Very strong. vi. Time of cane emergence — Early.
f. *Very young shoot.*—i. Anthocyanin coloration of apex during rapid growth — Very weak.
g. *Floricane* (*previous year's cane*).—i. Dormant cane color — Grayish brown-165A. ii. Fruiting lateral attitude — Semi-erect. iii. Fruiting lateral length — Medium-long 20-40 cm. iv. Average length — 120-150 cm.
h. *Prickles* (*spines*).—i. Presence — Present. ii. Density — Medium. iii. Length at 1 inch in height at end of harvest (from base to tip) — Medium. iv. Color — Purplish-brown-59A.
i. *Fruit storage life and shipping quality.*—Good.
j. *Market use.*—Fresh fruit.
k. *Hardiness zone* (*heat/cold tolerance*).—Wide. USDA zone 8-10.
l. *Plant/fruit disease and pest resistance/susceptibility.*—Low vulnerability for mildew and low vulnerability for spider mite.

m. *Petiole*.—i. Average Length — 8-12 cm. ii. Surface Texture — Rough. iii. Color — Light grayish green-191A.

LEAVES

General:

a. *Predominant number of leaflets.*—Equally 3-5.
b. *Profile of leaflets in cross section.*—Concave.
c. *Leaf rugosity.*—Weak.
d. *Color of upper side.*—Dark green-137A.
e. *Color of lower side.*—Light greyish green-191A.
f. *Surface texture of upper side.*—Weak rugosity.
g. *Terminal leaflet.*—i. Length — Long. 5-8 cm. ii. Width — Medium. 4-6 cm. iii. Length/width ratio — Medium. iv. Margin — Serrate. v. Overall shape — Rounded oval. vi. Apex shape — Cuspidate. vii. Base shape — Rounded.
h. *Later leaflets.*—i. Length — Long. 5-8 cm. ii. Width — Medium. 4-6 cm. iii. Length/width ratio — Medium. iv. Relative position of lateral leaflets — Free. v. Margin — Serrate. vi. Overall shape — Oval. vii. Apex shape — Cuspidate. viii. Base shape — Rounded.

FLOWERS

General:

a. *Diameter.*—Medium. 1-2 cm.
b. *Petal.*—i. Length — Medium. 6-10 mm. ii. Width — Medium. 2-4 mm. iii. Length/width — Medium. iv. Color of upper side — 155C. v. Color of lower side — 155C.
c. *Peduncle.*—i. Anthocyanin coloration — Absent. ii. Average Length — 2-5 cm. iii. Surface Texture — Rough. iv. Color — Light greyish green-191A.
d. *Pedicle*.—i. Average Length — 1-3 cm. ii. Surface Texture — Rough. iii. Color — Light greyish green-191A.

FRUIT

General:

a. *Length.*—Long. 25-35 mm.
b. *Diameter.*—Broad. 15-20 mm.
c. *Length/width ratio.*—Medium.
d. *General shape in lateral view.*—Broad conical.
e. *Color.*—Light red-34A.
f. *Glossiness.*—Strong.
g. *Firmness.*—Strong.
h. *Adherence to plug.*—Medium.
i. *Size of single drupe.*—Small.
j. *Number of drupelets per berry.*—Very high. 80-150.
k. *Average weight per berry.*—6-7 grams.

PRODUCTION

General:

a. *Main bearing type.*—Double crop.
b. *Primocane* (*current year's cane*).—i. Time of beginning of flowering — Early-Medium. 16-20 weeks after planting. ii. Time of beginning of fruit ripening — Medium. 3-4 weeks after planting. iii. Length of fruiting period — Medium. 8-10 weeks. iv. Yield — Very high. 25-35 T/Ha. v. Average number current season's cane — 4-5.
c. *Floricane* (*previous year's cane*).—i. Time of vegetative bud burst — Early-medium. 2-3 weeks after cutback. ii. Time of beginning of flowering — Medium. 8-10 weeks after bud break. iii. Time of beginning of fruit ripening — Early-medium. 4-5 weeks after flowering. iv. Length of fruiting period — Medium. 8-9 weeks. v. Yield — Very high. 25-35 T/Ha.

SEED

General:

a. *Size*.—Standard. 0.5-1 mm.
b. *Shape*.—Oval.

The invention claimed is:

1. A new and distinct variety of raspberry plant named 'ABB 136', as illustrated and described herein.

* * * * *